United States Patent [19]

Liang

[11] Patent Number: 5,471,003
[45] Date of Patent: Nov. 28, 1995

[54] PURIFICATION OF CYCLOPROPANECARBOXALDEHYDE

[75] Inventor: Shaowo Liang, Kingsport, Tenn.

[73] Assignee: Eastman Chemical Company, Kingsport, Tenn.

[21] Appl. No.: 345,192

[22] Filed: Nov. 28, 1994

[51] Int. Cl.$^6$ .................... C07C 47/00; C07C 45/62
[52] U.S. Cl. .................... 568/420; 568/426; 568/492
[58] Field of Search .................... 568/420, 426, 568/438, 449, 492

[56] References Cited

U.S. PATENT DOCUMENTS

| | | | |
|---|---|---|---|
| 4,273,945 | 6/1981 | Heilen et al. | 568/420 |
| 4,275,238 | 6/1981 | Petree et al. | 564/446 |
| 4,450,300 | 5/1984 | Andrade et al. | 568/420 |
| 4,720,593 | 1/1988 | Fischer | 568/420 |

*Primary Examiner*—Werren B. Lone
*Attorney, Agent, or Firm*—J. Frederick Thomsen; Harry J. Gwinnell

[57] ABSTRACT

Disclosed is a process for the removal of crotonaldehyde impurity from cyclopropanecarboxaldehyde by the selective, catalytic hydrogenation of crotonaldehyde to butyraldehyde followed by distillation of the butyraldehyde from the cyclopropanecarboxaldehyde.

4 Claims, No Drawings

PURIFICATION OF CYCLOPROPANECARBOXALDEHYDE

This invention pertains to a process for the purification of cyclopropanecarboxaldehyde. More specifically, this invention pertains to a process for the removal of crotonaldehyde from cyclopropanecarboxaldehyde by the selective, catalytic hydrogenation of crotonaldehyde to n-butyraldehyde (n-butanal) followed by distillation of the butyraldehyde from the cyclopropanecarboxaldehyde.

Cyclopropanecarboxaldehyde is an important synthetic building block for introducing the cyclopropane group into chemical compounds such as human and veterinary pharmaceutical products and pesticides. See, for example, U.S. Pat. No. 4,275,238, WO 91/09849 and EP 0 408 034 A1. Cyclopropanecarboxaldehyde can be prepared by the thermal isomerization or rearrangement of 2,3-dihydrofuran according to the procedures described U.S. Pat. No. 4,275,238 and C. L. Wilson, J. Amer. Chem. Soc. 1947, 69, 3002. The procedure of U.S. Pat. No. 4,275,238 comprises passing 2,3-dihydrofuran through a column heated at 375° to 540° C.

The isomerization of cyclopropanecarboxaldehyde by the thermal isomerization of 2,3-dihydrofuran results in the formation of some crotonaldehyde ($CH_3CH=CHCHO$), e.g., in concentrations of 6 to 10 weight percent. Due to the boiling points of crotonaldehyde (b.p. 102° C.) and cyclopropanecarboxaldehyde (b.p. 99° C.), the removal of the former from the latter by distillation is virtually impossible. Purification of cyclopropanecarboxaldehyde derived from 2,3-dihydrofuran therefore presents an especially difficult problem.

It is known (J. Org. Chem., 1978, 43, 3985) that crotonaldehyde is reduced to butyraldehyde at 100° C. with 10% excess formic acid, 30% excess triethyl- or tri-n-butyl amine, and 1 mole percent of palladium in the form of 10% palladium on carbon in 84% yield after 8 hours of reaction time. The process requires an excess of amine and formic acid (b.p. 100° C.) which present additional purification problems and is not suitable for large scale manufacturing. U.S. Pat. No. 4,450,300 described a process of selective hydrogenation of crotonaldehyde to butyraldehyde using a specially prepared palladium on aluminum oxide catalyst. CS 131903 describes a similar catalytic process.

It is well known that catalytic hydrogenation of compounds containing the cyclopropane group results in ring opening of the cyclopropane ring. C. W. Woodworth et al. (J. Chem. Soc. Chem. Commun. 1968, 569) reports that hydrogenation of 1-(1-adamantyl)-1-methylcyclopropane under 3 atmospheres pressure and at 50° C. in the presence of platinum oxide and acetic acid resulted in complete cleavage of the cyclopropane ring. Other examples of palladium or platinum catalyzed hydrogenolysis of cyclopropane rings are reported in Chem. Abstracts 59:2749, hydrogenolysis of 1-methyl 2-α-furylcyclopropane and 1-cyclopropyl-2-(α-furyl)cyclopropane, using 15% palladium on carbon at 150° C.; Chem. Abstracts 59:5029, hydrogenolysis of 1,3-dimethyl-5-alkylbicyclo[3.1.0]hexanes, using 15% platinum on carbon. M. Bartok et al., J. Mol. Catal., 1992, 77, 313 and J. Mol. Catal., 990, 63, 43, report the hydrogenolysis of substituted cyclopropanes over platinum of silica and palladium on silica catalysts.

M. T. Wuesthoff et al., J. Org. Chem., 968, 33, 1311, describes attempts to selectively hydrogenate an alpha, beta unsaturated ketone (spiro[2.5]oct-4-en--6-one) to a saturated ketone (spiro[2.5]octan-6-one) in the presence of a cyclopropane ring in the molecule. When 5% palladium on carbon was used as the catalyst under various conditions, significant cleavage of the cyclopropane ring was reported. C. H. Heathcook et al. (Tetrahedron Lett., 1968, 51, 5339 and Tetrahedron Lett., 1968, 51, 5343) also describe the poor selectivities in the selective hydrogenation of the carbon-carbon double bond in allylic cyclopropane compounds using carbon-supported palladium, platinum and rhodium as catalysts. Cleavages of the cyclopropane ring were the major competitive side reactions.

The process of the present invention provides an economical and effective means for the purification of cyclopropanecarboxaldehyde contaminated with crotonaldehyde by the selective hydrogenation of the crotonaldehyde to butyraldehyde and distilling the butyraldehyde from the cyclopropanecarboxaldehyde. The process comprises the steps of:

(1) contacting a mixture comprising cyclopropanecarboxaldehyde and crotonaldehyde with hydrogen in the presence of a palladium, platinum or rhodium catalyst under hydrogenation conditions of temperature and pressure; and (2) subjecting the hydrogenated mixture from step (1) to distillation to remove butyraldehyde therefrom to obtain cyclopropanecarboxaldehyde substantially free of crotonaldehyde. The operation of the process results in the conversion of the crotonaldehyde to butyraldehyde without significant hydrogenolysis of the cyclopropyl ring. The boiling point of butyraldehyde (75° C.) permits its removal from the hydrogenated mixture by simple distillation procedures to yield high purity (>99% assay) cyclopropanecarboxaldehyde.

The catalysts which can be used in this invention are selected from palladium, platinum and rhodium, preferably palladium. The catalyst may be supported catalysts wherein palladium, platinum and/or rhodium metal is deposited on the surface of a suitable catalyst support material. Typical catalyst supports include carbon, alumina, silica, silica-alumina, titania, kieselguhr, molecular sieves, zeolites, and the like. The palladium, platinum and/or rhodium metal typically constitutes 0.05 to 20 percent, preferably 0.1 to 10 percent, of the weight of the supported catalyst. Catalysts comprising alloys of palladium and platinum, e.g. 8% palladium/2% platinum on carbon, may be used as can the oxides of palladium, platinum or rhodium. Selectivities of about 91 to 97% are obtained from 5% platinum on carbon. Rhodium on carbon usually gives slower reaction rates and therefore must be used in larger amounts to achieve acceptable reaction rates. Catalysts comprising palladium, platinum or rhodium modified or promoted with, for example, molybdenum, chromium, iron, zirconium, and/or cobalt also may be used in this process.

The selective, catalytic hydrogenation may be carried out in either a homogeneous mode of operation wherein the catalyst is soluble in the liquid mixture which is hydrogenated or, preferably, in a heterogeneous mode utilizing a catalyst which is insoluble in the liquid reaction mixture. The amount of catalyst used per unit of the mixture to be subjected to hydrogenation can vary substantially and will depend on such factors as the particular catalyst used, the amount of solvent present, the conditions used and the mode of operation.

The hydrogenation conditions of temperature and pressure in the process of this invention can vary substantially depending on several factors such as contact time with the catalyst, the amount of catalyst and the choice of solvent. Hydrogenation temperatures of about 10° to 110° C. may be used, although milder temperatures in the range of about 10° to 40° C. are advantageous to maximize conversion of crotonaldehyde to its reduced products and minimize the reduction of cyclopropanecarboxaldehyde. More preferably, the reaction is carried out at a temperature in the range of 15° to 30° C. Higher temperatures along with long reaction times may result in over reduction of crotonaldehyde and cyclopropanecarboxaldehyde as well. The hydrogenation process may be carried out using total pressures in the range of atmospheric or ambient pressure up to 70 bars absolute, preferably about 1.4 to 10 bars absolute, and more preferably at 2.4 to 8 bars absolute. As noted above, the optimum combination of temperature and pressure depends on other process variables but can be readily ascertained by those skilled in the art.

The process of this invention may be carried out in the absence or in the presence of an inert solvent or diluent. Examples of permissible solvents include water, aliphatic, cycloaliphatic and aromatic hydrocarbons such as cyclohexane, heptane, toluene, xylene and mixed xylene isomers, ethers such as tetrahydrofuran, alcohols such as methanol, ethanol and n-butanol, cyclopropanecarboxaldehyde or butyraldehyde.

The weight ratio of crotonaldehyde:cyclopropanecarboxaldehyde in the mixture which is hydrogenated may be up to about 30:70 but more typically is in the range of about 1:99 to 10:90. An important feature of the process of the present invention is that reduction virtually stops after consumption of the crotonaldehyde is complete. The selectivity of the hydrogenation step is in the range of 97–100%. Cyclopropanecarboxaldehyde remains substantially unattacked during the hydrogenation, e.g., the amount of cyclopropanecarboxaldehyde converted to other products during the hydrogenation typically is less than 1 mole percent. It has been found that some n-butanol is produced during the hydrogenation, especially when a platinum on carbon catalyst is used, due to further reduction of butyraldehyde. Also, the use of platinum on carbon under some conditions causes the formation of small amounts of cyclopropanemethanol.

The present invention typically results in the removal of all, or essentially all, e.g., at least 99 weight percent, of the crotonaldehyde/butyraldehyde from the cyclopropanecarboxaldehyde/crotonaldehyde mixture used in the purification process. For example, when the process is carried out at pressures of about 2.4 to 4.5 bar absolute and at temperatures in the range of about 15° to 30° C. in the presence of a 5% palladium on carbon catalyst and in the absence of added solvent, conversion of the crotonaldehyde is complete and recovery of cyclopropanecarboxaldehyde is virtually 100% (selectivity is greater than 99%). The hydrogenation of crotonaldehyde can be controlled selectively to stop at the stage of n-butyraldehyde without further reduction to n-butanol. This facilitates the distillation by simply distilling off the lower boiler n-butyraldehyde and leaving the pure cyclopropanecarboxaldehyde as desired product. These conditions can be handled conveniently in general purpose, glass-lined plant equipment.

The process may be carried out in a batch, semi-continuous or continuous mode of operation. For example, batch operation may comprise agitating a slurry of a metal catalyst in a mixture of cyclopropanecarboxaldehyde and crotonaldehyde, and, optionally, a solvent in a pressure vessel for a time sufficient to hydrogenate essentially all of the crotonaldehyde to butyraldehyde. The catalyst can be separated from the hydrogenated mixture by filtration and the components of the filtrate separated by distillation to give cyclopropanecarboxaldehyde having a purity greater than 99% (by GC). Thus, when using a catalyst slurry mode of operation, the purification process requires an intermediate catalyst separation step, e.g., by filtration between the hydrogenation and distillation steps.

A preferred mode of operation uses a fixed bed of a metal catalyst wherein crotonaldehyde is hydrogenated in the gas or, especially, liquid phase, optionally in the presence of an inert diluent or solvent. Liquid phase operation typically involves feeding a mixture comprising crotonaldehyde and cyclopropanecarboxaldehyde, optionally in the presence of an inert solvent-diluent to the top of a columnar pressure reactor containing one or more fixed beds of a metal catalyst. The reactant solution flows (trickles) over the catalyst bed in the presence of hydrogen at the desired temperature and pressure and the hydrogenated product exits the bottom of the reactor and is separated into its components by distillation.

The distillation step wherein butyraldehyde is distilled from the cyclopropanecarboxaldehyde can be carried out according to conventional procedures. The distillation may be performed at ambient pressure or under reduced pressure, e.g., a pressure from ambient down to 30 torr.

The process provided by the present invention is further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic spectrometry and gas chromatography-mass spectrometry in comparison to authentic samples purchased from Aldrich. Pressure is reported in the examples in bar absolute and percentages are by weight unless specified otherwise.

EXAMPLE 1

To a 250-mL pressure bottle was charged 1 g of 5% platinum on carbon catalyst followed by 20 mL of cyclohexane and 5 g of a mixture consisting of 91.6% cyclopropanecarboxaldehyde and 8.4% crotonaldehyde. The bottle was placed in a Parr shaker-type hydrogenation apparatus and purged with nitrogen, then with hydrogen. The bottle was pressurized to 4.46 bar with hydrogen and agitation begun. The mixture was maintained at 25° to 28° C. throughout the reaction period. After 3 hours, no further hydrogen uptake was observed. The reaction mixture was allowed to stir at the same conditions for additional 17 hours. After removal of the catalyst, GC analysis of the crude mixture showed (disregarding solvent): 83.46% cyclopropanecarboxaldehyde, 3.04% n-butyraldehyde, 1.99% n-butanol, 7.25% cyclopropylmethanol and 4.26% other high boilers. No crotonaldehyde was detected in the product mixture. The selectivity was 91.1%.

EXAMPLE 2

To a 250-mL pressure bottle was charged 2 g of 5% platinum on carbon catalyst and 50 g of a mixture consisting of 90.8% cyclopropanecarboxaldehyde and 8.3% crotonaldehyde. The bottle was placed in a Parr shaker type hydrogenation apparatus and purged with nitrogen, then with hydrogen. The bottle was pressurized to 4.46 bar with hydrogen and agitation begun. The mixture was maintained at 25° to 28° C. throughout the reaction period. Samples were taken at 16 hr and 38 hr. The selectivity was 97.4%. Results of GC analyses are listed in Table I wherein Time is total elapsed reaction time in hours, CPCA is cyclopropanecarboxaldehyde, CPM is cyclopropylmethanol, t-HCr is trans crotonaldehyde, and c-HCr is cis crotonaldehyde.

EXAMPLE 3

To a 250-mL pressure bottle was charged 8 g of 5% platinum on carbon catalyst and 100 g of a mixture consisting of 90.8% cyclopropanecarboxaldehyde and 8.3% crotonaldehyde. The bottle was placed in a Parr shaker type hydrogenation apparatus and purged with nitrogen, then with hydrogen. The bottle was pressurized to 4.46 bar with hydrogen and agitation begun. The mixture was maintained at 25° to 28° C. throughout the reaction period. Samples were taken at 8 hr and 15 hr. The selectivity was 97.2%. Results of GC analysis are listed in Table II wherein Time, CPCA, .CPM, t-HCr, and c-HCr have the meanings set forth in Example 2. After the removal of the catalyst, distillation of the crude product gave 99% pure cyclopropanecarboxaldehyde.

consisting of 88.9% cyclopropanecarboxaldehyde and 9.25% crotonaldehyde. The bottle was placed in a Parr shaker type hydrogenation apparatus and purged with nitrogen, then with hydrogen. The bottle was pressurized to 3.1 bar with hydrogen and agitation begun. The mixture was maintained at 20° to 25° C. over a reaction period of 2 hours. After the removal of the catalyst, GC analysis of the crude mixture showed 88.47 g of cyclopropanecarboxaldehyde and 7.71 g of butyraldehyde. No crotonaldehyde was detected. The selectivity was greater than 99%. Distillation of the product mixture gave 99% pure cyclopropanecarboxaldehyde.

EXAMPLE 7

To a 500-mL pressure bottle were charged 0.80 g of 5% palladium on carbon catalyst followed by 200 g of a mixture

TABLE I

| Time  | CPCA   | CPM   | t-HCr | c-HCr | n-Butanol | n-Butanal | Others |
|-------|--------|-------|-------|-------|-----------|-----------|--------|
| 0     | 90.80% | 0     | 2.81% | 5.50% | 0         | 0         | 0.91%  |
| 16 hr | 89.51% | 0.60% | 1.53% | 0     | 0.34%     | 3.96%     | 4.04%  |
| 38 hr | 88.42% | 1.23% | 0     | 0     | 0.57%     | 4.26%     | 5.46%  |

TABLE II

| Time  | CPCA   | CPM   | t-HCr | c-HCr | n-Butanol | n-Butanal | Others |
|-------|--------|-------|-------|-------|-----------|-----------|--------|
| 0     | 90.80% | 0     | 2.81% | 5.50% | 0         | 0         | 0.91%  |
| 8 hr  | 89.10% | 0.48% | 0.77% | 0     | 0.26%     | 3.94%     | 4.87%  |
| 15 hr | 88.26% | 0.69% | 0.19% | 0     | 0.33%     | 4.51%     | 5.42%  |

EXAMPLE 4

To a 250-mL pressure bottle was charged 0.01 g of 8% palladium/2% platinum on carbon catalyst followed by 10 g of tetrahydrofuran (THF) and 5 g of a mixture consisting of 89.8% cyclopropanecarboxaldehyde and 7.8% crotonaldehyde. The bottle was placed in a Parr shaker type hydrogenation apparatus and purged with nitrogen, then with hydrogen. The bottle was pressurized to 3.1 bar with hydrogen and agitation begun. The mixture was maintained at 20° to 25° C. over a reaction period of 30 minutes. After the removal of the catalyst, GC analysis of the crude mixture showed (disregarding solvent): 4.48 g of cyclopropanecarboxaldehyde, 0.34 g of butyraldehyde. No crotonaldehyde was detected. The selectivity was greater than 99%.

EXAMPLE 5

To a 250-mL pressure bottle was charged 0.01 g of 5% palladium on carbon catalyst followed by 10 g of THF and 5 g of a mixture consisting of 89.8% cyclopropane-carboxaldehyde and 8.0% crotonaldehyde. The bottle was placed in a Parr shaker type hydrogenation apparatus and purged with nitrogen, then with hydrogen. The bottle was pressurized to 3.1 bar with hydrogen and agitation begun. The mixture was maintained at 20° to 25° C. over a reaction period of 40 minutes. After the removal of the catalyst, GC analysis of the crude mixture showed (disregarding solvent): 4.48 g of cyclopropanecarboxaldehyde, 0.34 g of butyraldehyde. No crotonaldehyde was detected. The selectivity was greater than 99%.

EXAMPLE 6

To a 250-mL pressure bottle were charged 0.40 g of 5% palladium on carbon catalyst followed by 100 g of a mixture consisting of 75.58% cyclopropanecarboxaldehyde and 24.42% crotonaldehyde. The bottle was placed in a Parr shaker type hydrogenation apparatus and purged with nitrogen, then with hydrogen. The bottle was pressurized to 3.1 bar with hydrogen and agitation begun. The mixture was maintained at 30° to 38° C. over a reaction period of 1 hour. After the removal of the catalyst, GC analysis of the crude mixture showed 149.91 g of cyclopropanecarboxaldehyde and 35.90 g of butyraldehyde. No crotonaldehyde was detected. The selectivity was greater than 99%. Distillation of the product mixture gave 99% pure cyclopropanecarboxaldehyde. This example shows that the process is applicable to high concentrations of crotonaldehyde.

EXAMPLE 8

To a 250-mL pressure bottle was charged 0.5 g of 5% palladium on alumina followed by 10 g of a mixture consisting of 91.17% cyclopropanecarboxaldehyde and 7.88% crotonaldehyde. The bottle was placed in a Parr shaker type hydrogenation apparatus and purged with nitrogen, then with hydrogen. The bottle was pressurized to 3.1 bar with hydrogen and agitation begun. The mixture was maintained at 25° to 28° C. over a reaction period of 35 minutes. After the removal of the catalyst, GC analysis of the crude mixture showed 8.48 g of cyclopropanecarboxaldehyde, 1.28 g of butyraldehyde and 0.03 g n-butanol. No crotonaldehyde was detected. The selectivity was 93%.

EXAMPLE 9

To a 250-mL pressure bottle were charged 0.05 g of 5% palladium on alumina catalyst followed by 10 g of a mixture consisting of 90.46% cyclopropanecarboxaldehyde and 7.97% crotonaldehyde. The bottle was placed in a Parr shaker type hydrogenation apparatus and purged with nitrogen, then with hydrogen. The bottle was pressurized to 3.1 bar with hydrogen and agitation begun. The mixture was maintained at 25° to 28° C. over a reaction period of 40 minutes. After the removal of the catalyst, GC analysis of the crude mixture showed 9.02 g of cyclopropanecarboxaldehyde, 0.59 g of butyraldehyde. No n-butanol and crotonaldehyde were detected. The selectivity was greater than 99%.

EXAMPLE 10

To a 250-mL pressure bottle was charged 0.1 g of 5% rhodium on carbon catalyst followed by 10 g of a mixture consisting of 91.90% cyclopropanecarboxaldehyde and 8.10% crotonaldehyde. The bottle was placed in a Parr shaker type hydrogenation apparatus and purged with nitrogen, then with hydrogen. The bottle was pressurized to 4.8 bar with hydrogen and agitation begun. The mixture was maintained at 25° to 28° C. over a reaction period of 2 days. After the removal of the catalyst, GC analysis of the crude mixture showed 91.10% of cyclopropanecarboxaldehyde, 0.23% of butyraldehyde and 4.10% crotonaldehyde remained. The selectivity was greater than 99%.

EXAMPLE 11

To a 250-mL pressure bottle was charged 2 g of 5% rhodium on carbon catalyst and 10 g of a mixture consisting of 90.46% cyclopropanecarboxaldehyde and 7.97% crotonaldehyde. The bottle was placed in a Parr shaker type hydrogenation apparatus and purged with nitrogen, then with hydrogen. The bottle was pressurized to 3.1 bar with hydrogen and agitation begun. The mixture was maintained at 25° to 28° C. over a reaction period of 20 minutes. After the removal of the catalyst, GC analysis of the crude mixture showed 9.0 g of cyclopropanecarboxaldehyde, 0.48 g of butyraldehyde and 0.02 g n-butanol. No crotonaldehyde was detected. The selectivity was greater than 99%.

EXAMPLE 12

To a 500-mL pressure bottle was charged 1.0 g of 5% palladium on carbon followed by 300 g of a mixture consisting of 87.85% cyclopropanecarboxaldehyde and 10.80% crotonaldehyde). The bottle was placed in a Parr shaker type hydrogenation apparatus and purged with nitrogen, then with hydrogen. The bottle was pressurized to 3.1 bar with hydrogen and agitation begun. The mixture was maintained at 20° to 25° C. over a reaction period of 6 hours. GC analysis of the crude product mixture showed 262.02 of cyclopropanecarboxaldehyde and 31.26 g of butyraldehyde. Neither crotonaldehyde nor n-butanol was detected. The selectivity was greater than 99%. After removal of the catalyst by filtration, the crude product was distilled under atmospheric pressure using a 1 meter column packed with Penn State packing to obtain 251.53 g of cyclopropanecarboxaldehyde having a purity of 99%.

The invention has been described in detail with particular reference to preferred embodiments thereof, but it will be understood that variations and modifications can be effected within the spirit and scope of the invention.

I claim:

1. Process for the purification of cyclopropanecarboxaldehyde contaminated with crotonaldehyde comprising the steps of:

(1) contacting a mixture comprising cyclopropanecarboxaldehyde and crotonaldehyde with hydrogen in the presence of a palladium, platinum or rhodium catalyst under hydrogenation conditions of temperature and pressure; and (2) subjecting the hydrogenated mixture from step (1) to distillation to remove butyraldehyde therefrom to obtain cyclopropanecarboxaldehyde substantially free of crotonaldehyde.

2. Process according to claim 1 wherein the hydrogenation conditions of temperature and pressure comprise a temperature of about 10° to 100° C. and a pressure of about ambient to 70 bar absolute.

3. Process for the purification of cyclopropanecarboxaldehyde contaminated with crotonaldehyde comprising the steps of:

(1) contacting a mixture comprising cyclopropanecarboxaldehyde and crotonaldehyde in a crotonaldehyde:cyclopropanecarboxaldehyde weight ratio of about 1:99 to 10:90 with hydrogen in the presence of a palladium catalyst at a temperature of about 10° to 40° C. and a pressure of about 1.4 to 10 bar absolute; and (2) subjecting the hydrogenated mixture from step (1) to distillation to remove butyraldehyde therefrom to obtain cyclopropanecarboxaldehyde substantially free of crotonaldehyde.

4. Process according to claim 3 wherein the catalyst is palladium on carbon or palladium on alumina wherein the palladium constitutes about 0.1 to 10 weight percent of the catalyst.

* * * * *